United States Patent [19]
Morcom

[11] Patent Number: 5,694,448
[45] Date of Patent: Dec. 2, 1997

[54] IMAGING APPARATUS

[75] Inventor: Christopher John Morcom, Maldon, United Kingdom

[73] Assignee: EEV Limited, Chelmsford, United Kingdom

[21] Appl. No.: 679,517

[22] Filed: Jul. 12, 1996

[30] Foreign Application Priority Data

Aug. 1, 1995 [GB] United Kingdom ............. 9515762

[51] Int. Cl.$^6$ .................. H04N 3/15; A61B 6/14
[52] U.S. Cl. .................. 378/98.8; 378/98.7
[58] Field of Search ............. 378/98.8, 91, 95, 378/96, 97, 168, 207; 250/363.01, 370.01, 370.08, 370.09, 370.15; 348/162, 243, 244, 294, 297, 298

[56] References Cited

U.S. PATENT DOCUMENTS 4,437,743  3/1984  Sakai et al. .
5,053,873  10/1991  Taniji .
5,513,252  4/1996  Blaschka et al. ............. 378/98.8

FOREIGN PATENT DOCUMENTS 8909398  11/1994  Germany .
WO 93/23952  11/1993  WIPO .

*Primary Examiner*—David P. Porta
*Attorney, Agent, or Firm*—Spencer & Frank

[57] ABSTRACT

In imaging apparatus particularly for use in intra-oral dental applications, a solid state imager is continually clocked out during a wait period prior to irradiation from an X-ray source. A signal derived from the CCD is compared with a threshold at to determine the onset of irradiation by the X-ray source which will appear as a rapid change in the signal level. The threshold conditions are varied to follow changes in ambient conditions and particularly temperature changes to allow for increase of dark current with a rise in temperature. This permits the threshold at which the CCD is triggered to begin image acquisition to be set at a relatively low level whilst minimising the risk of false triggering.

12 Claims, 3 Drawing Sheets

IMAGING APPARATUS

FIELD OF THE INVENTION

This invention relates to imaging apparatus and more particularly to solid state imagers which include radiation sensitive detector elements.

BACKGROUND OF THE INVENTION

It has been proposed to use CCDs and other types of solid state detectors for dental and other medical applications using X-ray irradiation to examine structural features of a patient. The CCD device replaces the film used in previous systems and enables real-time imaging to be achieved together with a more controlled lower dosage of X-rays for a given exposure.

In one known arrangement, a CCD device is used intra-orally and is electrically connected to an X-ray source. When the X-ray source is energised, a start signal is transmitted along the connecting wire to the CCD device and to its control circuitry to begin image acquisition and read-out. In other arrangements, the X-ray source and CCD device have no physical connection. A supplementary sensor is arranged close to the imaging area of the CCD to detect the onset of X-ray energy. On detection of the incident X-ray energy, the sensor sends a signal to the CCD control circuitry to cause imaging to begin.

In another arrangement, the CCD device is continually read-out prior to irradiation by X-rays. A signal derived from the CCD is compared with a reference level. If it exceeds the reference level, the image acquisition phase of the CCD operation is initiated.

The present invention seeks to provide an improved imaging apparatus which is particularly advantageously used for dental X-ray diagnosis where the imager device is located intra-orally but it is envisaged that it may also be used in other medical or diagnostic applications and could also be advantageously employed for non-medical applications.

SUMMARY OF THE INVENTION

According to the invention, there is provided imaging apparatus comprising a solid state imager device including radiation sensitive detector elements; means for using a signal derived from the detector elements in a threshold test; means for initiating image acquisition when the threshold test is satisfied; and means for varying a threshold condition with changes in ambient conditions.

Solid state devices such as CCDs suffer from the generation of a thermally based signal known as dark current. During a wait period, for example, in an X-ray system before X-ray exposure, the imager device generates dark current which uses signal handling capacity of the device and may even totally fill that capacity leaving no space for signal information. When onset of X-rays begins therefore, the device must be emptied of the charge it holds due to noise to enable image acquisition to be initiated.

Dark current approximately doubles every 7° C. in silicon devices and in dental use, CCDs may be used with an operating temperature of up to 40° C. In the previously known arrangement in which the signal output is compared with a reference level, it is therefore necessary to set this reference at a relatively high level to allow for signals arising from 40° C. dark current and other noise features. This is significant given the exponential rise in dark current with temperature. If the reference is set too low, a false trigger signal may result causing a failed image and requiring the patient to be subjected to a repeat exposure.

By employing the invention, a threshold test is used which may be continually varied to accommodate changes in ambient conditions. Hence, the threshold level need not be set initially at a high level unless ambient conditions so require. Immediately prior to a particular X-ray exposure, the CCD may subjected to a temperature of only 20° C., say, and not 40° C. which may be encountered after some time or not at all although in theory this temperature might be attained. As the level is minimised to that required for the particular conditions encountered the onset of X-ray radiation is more quickly and reliably determined than in the previously known system. Hence the dosage of X-ray radiation to which the patient is subjected is also minimized as image acquisition is started nearer the beginning of the X-ray pulse. A rapid change in the signal derived from the detector elements indicates the onset of the radiation to be imaged and causes image acquisition to be begin. The signal may be derived directly from the detector elements or may be processed in some way first.

The invention is particularly advantageously used for X-ray irradiation of patients for dental and other medical uses such as mammography as it allows X-ray dosages to be reduced to the minimum level required. This meets stringent health and safety requirements by avoiding unnecessary exposure to X-ray radiation which is not used in the production of an image without increasing the risk of image failure with the need to repeat the procedure.

Although the invention is particularly useful for dental applications because of the temperature constraints, other medical applications may also with advantage employ it. Also, the invention may be employed, for example, in non-X-ray imaging arrangements such as where optical radiation is to be monitored or for other types of high energy radiation.

The change in the threshold condition in most cases will occur because of variations in the ambient temperature. However, in some applications, ambient background illumination may be monitored and the threshold varied accordingly. A further benefit of the invention is that the threshold will also be varied to take into account the increase in dark current which occurs in solid state imagers when exposed to ionising radiation such as X-rays.

In one particularly advantageous embodiment of the invention the means for varying the threshold condition with changes in ambient conditions includes comparing a signal derived from the detector elements with a threshold level and changing the threshold level in accordance with changes in the detected signal. In another arrangement, a signal derived from the detector elements is compared with a previously derived signal to give a difference over a known short time interval and the difference is compared with a set threshold level. Although in this case, the threshold level is set at a fixed value, the comparison to determine the difference in previous and current signals is used to compensate for changes in temperature and hence changes the threshold condition.

BRIEF DESCRIPTION OF THE DRAWINGS

Some ways in which the invention may be performed are now described with reference to the accompanying drawings in which.

DESCRIPTION OF PREFERRED EMBODIMENTS

Figure 1:
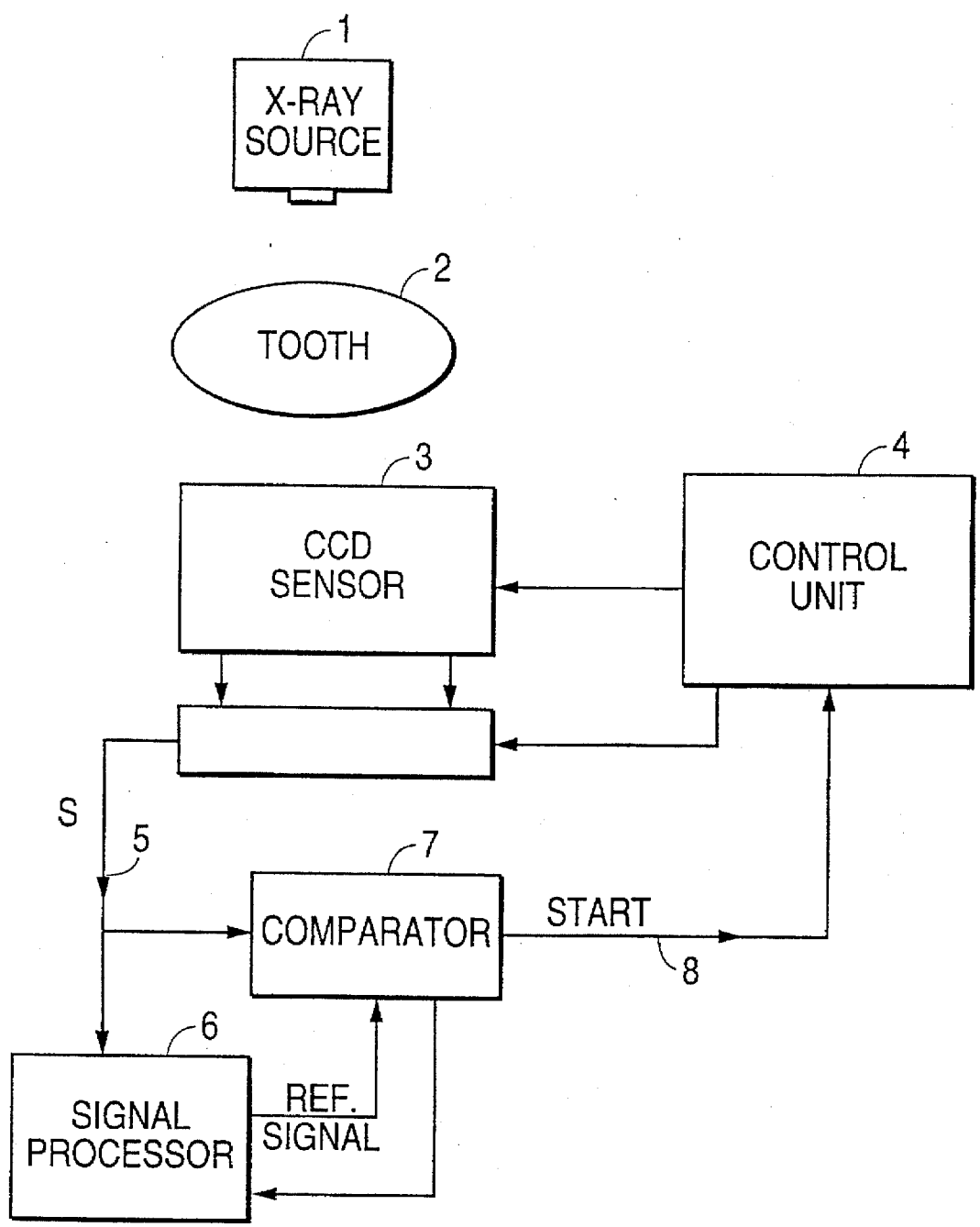
FIG. 1 schematically illustrates an X-ray imaging arrangement for intra-oral dental use.

With reference to FIG. 1, an X-ray source 1 is arranged to irradiate a tooth or other object 2 to be imaged behind which is located a CCD sensor device 3. The CCD device 3 comprises an array of radiation sensitive detector elements which accumulate charge depending on the intensity of the radiation which is incident thereon. By applying control signals from a control unit 4 the accumulated charge can be clocked from the sensor elements at selected times to produce a signal S on an output line 5 which is representative of the radiation pattern falling on the detector 3. In the absence of radiation, the signal S will essentially be due to dark current and other noise.

The signal S is applied to signal processing circuit 6 and to a comparator 7. The comparator 7 performs a comparison test to determine if there is a rapid change in the magnitude of the signal, which indicates that the X-ray source 1 has been switched on. When this occurs, a start signal is transmitted along output line 8 to the control unit 4 to begin image acquisition by the device 3. Prior to the irradiation with the X-ray source, the control unit 4 applies potentials to the CCD electrodes to continually clock out the charge accumulating at the sensor elements on line 5. The comparator 7 is also connected to apply a signal the signal processor 6 to enable it to accept the signal information for image processing when the test indicates that the X-ray source is irradiating the object 2.

Figure 2:
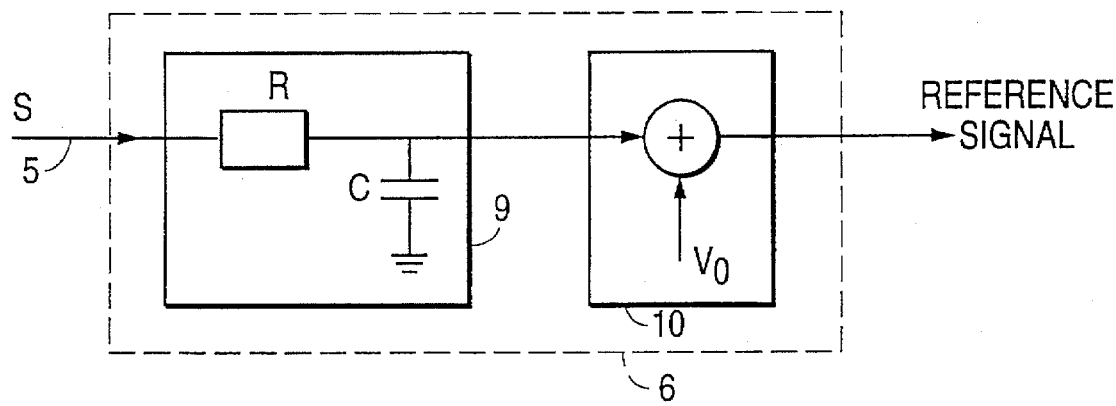
FIG. 2 schematically shows in greater detail part of the arrangement shown in FIG. 1.

FIG. 2 illustrates part of the signal processor 6 in more detail. The signal S on line 5 is first applied to a low pass filter 9 with a long time constant. This removes any short term fluctuations from the signal, including the effect of the X-ray pulse, and provides a signal which tracks the long term average of signal S as ambient conditions vary.

A positive offset (Vo) is then applied to the low pass filtered signal by an offset circuit 10 to generate a reference signal which is then passed to the comparator 7.

Under normal conditions the output of the comparator 7 will be low due to the offset voltage Vo. However, when an X-ray pulse is applied, signal S will rise rapidly. The action of the low pass filter 9 prevents the reference signal from rising quickly and hence the output of the comparator will switch high indicating that image acquisition should begin.

The comparator 7 continues receiving a signal on line 5 during image acquisition and also detects when the X-ray source is switched off at the end of the irradiation period.

Figure 3:
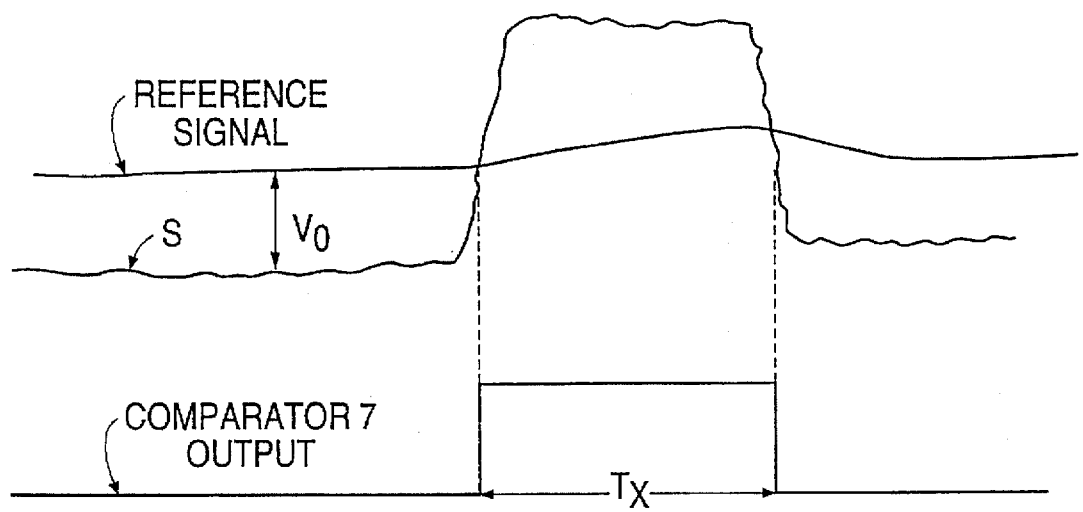
FIG. 3 is an explanatory diagram relating to the operation of the arrangement of FIG. 1.

FIG. 3 is an explanatory diagram which illustrates the operation of the arrangement of FIG. 1. The time consent of the filter 9 is chosen to be significantly greater than the duration Tx of the transmitted X-ray pulse.

Figure 4:
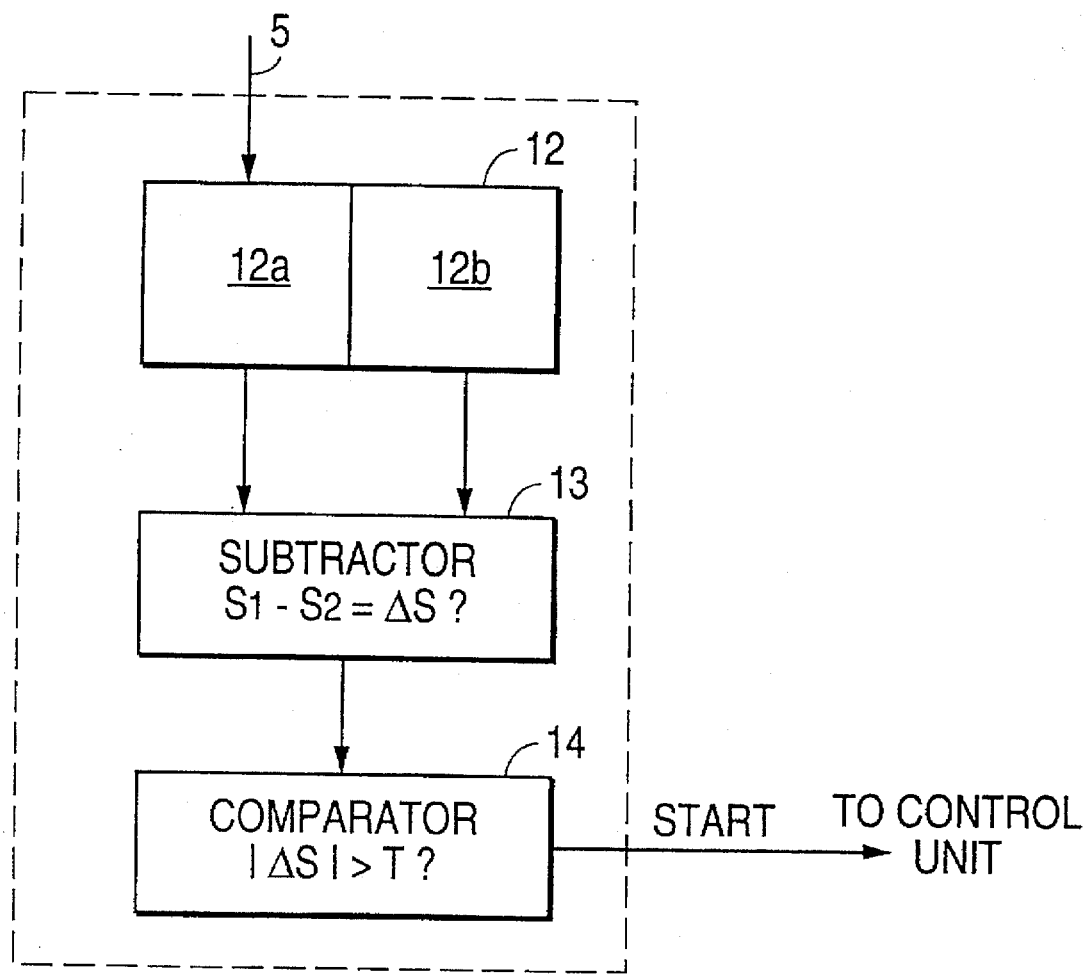
FIG. 4 shows part of an alternative arrangement in accordance with the invention.

FIG. 4 illustrates an alternative arrangement used for giving a continuously variable threshold level which may be used in place of the comparator 7 of FIG. 1. In this arrangement, the signal S on line 5 derived from the CCD output is applied to a storage means 12 having two sections 12a and 12b. The current signal magnitude is stored in part 12a of the store and the previous value is shifted to part 12b. The two signal magnitudes are subtracted at 13 to give a difference showing the change in magnitude of the signal over the time between the two samples. This is compared with a fixed threshold value T at comparator 14. The level T is set at a value which is greater than would be expected for changes between the two signal values due solely to thermal effects and other changes in ambient conditions but is significantly smaller than a change which would occur on the onset of irradiation with X-rays. The output of the comparator 14 is applied to the control unit 4 to begin image acquisition when the onset of X-ray irradiation is detected. In this case, therefore, although the threshold value T is fixed, the signal which is compared with it is continually varied in accordance with changes due thermal effects and other noise considerations and thus the conditions of the threshold test are variable with changes in the ambient conditions.

What is claimed is:

1. Imaging apparatus comprising: a solid state imager device including radiation sensitive detector elements; means for carrying out a threshold test; means for varying a threshold condition of the threshold test in accordance with changes in ambient conditions; and means for initiating image acquisition by said imager device when said threshold test is satisfied.

2. Imaging apparatus as claimed in claim 1 includes means for comparing a signal derived from said detector elements with a threshold level.

3. Imaging apparatus as claimed in claim 2 wherein said means for varying a threshold condition includes comparison means for comparing a signal derived from said detector elements with a threshold level and changing said threshold level in accordance with changes in said signal.

4. Apparatus as claimed in claim 2 wherein said means for varying a threshold condition includes comparison means for comparing a signal derived from said detector elements with a previously obtained signal from said detector elements to give a difference value and said difference value being compared with a threshold level.

5. Apparatus as claimed in claim 1 wherein said solid state imager device is a CCD device.

6. Apparatus as claimed in claim 1 wherein said apparatus is adapted for use in an intra-oral arrangement.

7. Apparatus as claimed in claim 1 wherein said imager device, in use, detects X-ray radiation.

8. Apparatus as claimed in claim 3 wherein said solid state imager device is a CCD device.

9. Apparatus as claimed in claim 4 wherein said solid state imager device is a CCD device.

10. Apparatus as claimed in claim 1 and including an X-ray source for irradiating a subject behind which said solid state imager device is located during use.

11. Apparatus as claimed in claim 1 and including means for substantially continually clocking out charge from said detector elements prior to initiating image acquisition.

12. A dental X-ray imaging apparatus comprising: an X-ray source arranged in use to irradiate a subject; a solid state imager device for receiving X-ray radiation from said source after it has passed through said subject; means for initiating image acquisition when a threshold test is satisfied which incudes means for comparing a signal derived from said imager with a threshold condition; and means for varying said threshold condition in accordance with changes in ambient conditions.

* * * * *